United States Patent [19]

Schröder et al.

[11] Patent Number: 5,059,687

[45] Date of Patent: Oct. 22, 1991

[54] PROCESS FOR THE CONDENSATION OF IMIDES AND ALCOHOLS OR AMINES

[75] Inventors: Christiaan Schröder, Stein; Albert A. Van Geenen, Brunssum; Josefina M. A. Schiffer, Vaals, all of Netherlands of Netherlands

[73] Assignee: Stamicarbon B.V., Geleen, Netherlands

[21] Appl. No.: 507,851

[22] Filed: Apr. 12, 1990

[30] Foreign Application Priority Data

Apr. 14, 1989 [NL] Netherlands .................. 8900937

[51] Int. Cl.$^5$ ................ C07D 233/38; C07D 207/273; C07D 211/40
[52] U.S. Cl. .................................... 540/526; 540/529; 540/451; 540/452; 540/487; 546/14; 546/21; 546/243; 548/406; 548/412; 548/550
[58] Field of Search ............... 540/487, 526, 529, 451, 540/452; 546/14, 21, 243; 548/406, 412, 550

[56] References Cited

U.S. PATENT DOCUMENTS

| | | | |
|---|---|---|---|
| 3,944,629 | 3/1976 | Hedrick | 540/529 |
| 4,678,839 | 7/1987 | Hallgren et al. | 525/390 |

FOREIGN PATENT DOCUMENTS 62182378  1/1989  Japan .................... 548/550

*Primary Examiner*—Robert T. Bond
*Attorney, Agent, or Firm*—Cushman, Darby & Cushman

[57] ABSTRACT

A process for the condensation of imides and alcohols or amines to ester acyl lactams, ester amide acyl lactams or amide acyl lactams by reacting a polyol or polyamine in the liquid phase with an acyl lactam compound is disclosed.

12 Claims, No Drawings

PROCESS FOR THE CONDENSATION OF IMIDES AND ALCOHOLS OR AMINES

BACKGROUND OF THE INVENTION

1. Field of the Invention

The present invention relates to a process for the condensation of imides and alcohols or amines to ester acyl lactams, ester amide acyl lactams or amide acyl lactams by reacting a polyol or polyamine in the liquid phase with an acyl lactam.

2. Background Information

U.S. Pat. No. 3,922,254 describes a process in which an imide and an alcohol are condensed in the presence of a metal or a metal compound, the metal being selected from group IA, IIA, IIB or IIIA of the Periodic Table of the elements. In this process the degree of conversion obtained for the condensation product of the imide and alcohol is 75–80 wt. %.

SUMMARY OF THE INVENTION

An object of the invention is to provide a simple process for the condensation of imides and alcohols or amines with a greatly improved degree of conversion.

Broadly, according to the invention, a process is provided for the condensation of imides and alcohols or amines comprising reacting a polyol or polyamine and acyl lactam in the presence of a lactam or lactone.

In one embodiment, the invention is directed to a process for the condensation of imides and alcohols or amines to form ester acyl lactams, amide acyl lactams or ester amide acyl lactams comprising the steps of reacting a polyol or a polyamine, in the liquid phase, with an acyl lactam and condensing in the presence of a lactone or a lactam with fewer than 7 ring atoms or a compound containing a lactam group with fewer than 7 ring atoms.

DETAILED DESCRIPTION OF THE INVENTION

As noted above, the invention relates to the condensation of imides and alcohols or amines to form ester acyl lactams, ester amide acyl lactams or amide acyl lactams by reacting a polyol or a polyamine and an acyl lactam in the presence of a lactone or a lactam with fewer than 7 ring atoms, in the liquid phase.

The term 'acyl lactam' is understood to mean a compound with the following formula:

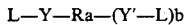

wherein:

L is a lactam ring, and preferably caprolactam,

Y and Y' are both acyl groups, and preferably

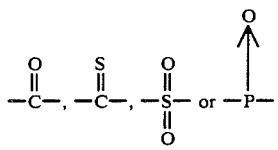

R is an alkyl, aralkyl, alkylaryl or aryl group which is straight chained, branched or cyclic, a is a number greater than or equal to 0 and b is a number greater than or equal to 1.

Examples of suitable acyl lactam compounds include terephthaloyl biscaprolactam, adipoyl biscaprolactam, oxalyl biscaprolactam, isophthaloyl biscaprolactam, isophthaloyl bispyrrolidone, isophthaloyl caprolactam pyrrolidone and the like, and mixtures thereof.

In the process according to the invention, compounds with the following formula may be formed:

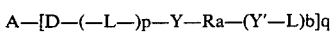

wherein:

D is an oxygen atom or an NH group,

A is a radical formed from a polyol or a polyamine with the formula A-(DH)q in which q is a number greater than or equal to 2, p is a number greater than or equal to 0, (—L—) is an open lactam (block) and L, Y, Y', R, b and a are as indicated above.

The value of p may differ for each acyl lactam group bound to the polyol or polyamine, depending on the reaction conditions. This in turn depends upon whether the lactam group is split off or subjected to a ring opening reaction. If the lactam group is split off from acyl lactam, p is equal to 0. If the lactam group is subjected to a ring opening reaction, p is equal to 1. However, in certain cases it may be advantageous if a relatively small, polyamide block is formed between the polyol or polyamine and the acyl lactam.

In the process according to the invention, polyols with the following general formula are used:

in which q is a number greater than or equal to 2, and preferably between 2 and 4.

The A group in the A—(OH)q formula can be a hydrocarbon (preferably with a molecular weight of at least 28), a polyether or a polysiloxane group. The molecular weights of polymers or polymer segments, are number average molecular weights which can be determined by known methods such as gel-phase chromatography. The polysiloxane groups or polysiloxane segments, are groups or segments containing at least 50 wt. % of one or more units with the following formula:

in which B stands for straight chain or branched alkyl, aryl, aralkyl, alkaryl or cycloalkyl groups.

Further, the polysiloxane groups or segments can also contain other groups, including, for example ether groups with lower alkyl groups containing 1–5 carbon atoms such as ethane or methane. Such ether groups are terminal groups comprising a chain of repeating siloxane units. These ether groups account for up to 50 wt. %, but preferably less than 30 wt. %, of the polysiloxane group. However, A is preferably a hydrocarbon group or a polyether group. Examples of hydrocarbon groups include alkylene groups, diols, for example, ethylene glycol, or polymeric hydrocarbons, for example, segments of polybutadiene containing two or more hydroxyl groups. A polyoxypropylene segment containing two or more hydroxyl groups is an example of a polyether group.

Examples of compounds containing hydroxyl groups in the aforementioned process include ethylene glycol, propylene glycol, poly(oxybutylene) glycol, poly(oxyethylene) glycol, poly(oxypropylene) diol, poly(oxypropylene) triol, poly(oxypropylene) tetrol, polybutadiene diol, polydimethyl siloxanes containing hydroxyl groups and combinations thereof, such as block polymers of poly(oxypropylene) and poly(oxyethylene) containing hydroxyl groups.

However, it is also possible to use a polyol obtained by ethoxylation or propoxylation of, including, for example, ethylene diamine, glucose, fructose, and saccharose and the like.

The aforementioned polyols are polymeric polyols having an average molecular weight of at least 62, preferably at least 1000, more preferably between 2000 and 10,000.

The polyamines include polyamines with at least two amine groups and preferably selected from the group consisting of polyoxyalkylene polyamines, polyalkadiene polyamines, polyalkene polyamines and combinations thereof.

The polyamine has an average molecular weight between 300 and 10,000, preferably at least 500, and most preferably at least 1000, and is selected so that the polyamine is incorporated into the elastomeric segment of the polyamide, while the lactam polymerization is incorporated into the hard crystalline segment of the polyamide. Elastomeric segments incorporated in the nylon block copolymer provide a glass transition temperature (Tg) of less than 0° C., preferably less than −25° C. The glass transition temperature is determined by differential scanning calorimetry under nitrogen, at a scan rate of 10°–20° C. per minute. The number of elastomeric segments in the nylon block copolymer according to the present process may vary from 10 weight percent to 90 weight percent, depending on the desired properties.

Examples of suitable polymeric hydrocarbon polyamines include, for example, polybutadiene diamine, polybutadiene polyamines and butadiene acrylonitrile polyamines. Examples of suitable polyether polyamines are poly(oxybutylene) diamine, poly(oxyethylene) diamine, poly(oxypropylene) diamine, poly(oxypropylene) triamine, poly(oxypropylene) tetramine and combinations thereof, such as block copolymers of poly(oxypropylene) and poly(oxyethylene) with at least two functional amine groups and are most preferably poly(oxypropylene) triamines with an average molecular weight of at least 2000.

The process is carried out at temperature ranges from about 80° C. to about 150° C.

The reaction is preferably carried out in the liquid phase, and in the absence of a solvent. However, the reaction may be carried out in a solvent that is inert with respect to the reagents. Further, mixtures of a lactam and a inert solvent or a mixture of different lactams may be used.

The reaction is carried out in the presence of a lactone, a lactam with fewer than 7 ring atoms, or a compound containing a lactam group with fewer than 7 ring atoms and include pyrrolidone, capro-lactone, 3-methylpyrrolidone, butyro-lactone, N-methylpyrrolidone, valero-lactam, isophthaloyl caprolactampyrrolidone and isophthaloyl bispyrrolidone and the like and mixtures thereof. The reaction is preferably carried out in the presence of pyrrolidone.

The amount of lactone and/or lactam added is between 0.01 and 15 wt. %, preferably between 0.1 and 10 wt. %, and most preferably between 1 and 5 wt. % based upon the total weight of reactants.

The ester acyl lactams and/or ester amide acyl lactams which are formed are highly suitable for use as activators in the preparation of nylon polymers, in particular the RIM (Reaction Injection Moulding) systems, in which it is desirable for the polymerization to take place within a very short period of time.

The invention is further described in the following detailed examples.

COMPARATIVE EXAMPLE A AND EXAMPLES I-IV 336 grams of ethylene oxide capped polyoxypropylene triol (MW 4480) and 80 grams of isophthaloyl biscaprolactam are combined in a reactor and stirred for 24 hours at 140° C., in the presence of pyrrolidone. The degree of conversion for these reactions are shown in Table I below.

TABLE I

| reaction time (hours) ↓ | Example |
|---|---|---|---|---|---|
| | A | I | II | III | IV |
| | pyrrolidone content (wt. %) | | | | |
| | 0 | 1.8 | 3 | 5 | 10 |
| 1 | 31.5 | 58.8 | 56.9 | 52.4 | 53.0 |
| 2 | 55.5 | 68.8 | 73.3 | 69.5 | 68.1 |
| 3 | 66.6 | 73.8 | 80.3 | 75.3 | 77.7 |
| 5 | 75.3 | 81.5 | 84.0 | 82.7 | 86.7 |
| 7 | 77.7 | 90.0 | 86.8 | 85.0 | 91.0 |
| 24 | 80.0 | 92.5 | 92.5 | 92.5 | 98.8 |

EXAMPLE V 336 grams of ethylene oxide (EO) capped polyoxypropylene triol (MW 4480) and 68 grams of isophthaloyl bispyrrolidone were heated in a reactor for 24 hours at 140° C. Initially, after 7 hours, the degree of conversion was 88% and after 24 hours, it had increased to 98.8%.

EXAMPLE VI 336 grams of EO capped polyoxypropylene triol (MW 4480) and 74 grams of isophthaloyl caprolactam pyrrolidone were heated in a reactor for 24 hours at 140° C. Initially, after 7 hours the degree of conversion was 86% and after 24 hours, it had increased to 97.5%.

COMPARATIVE EXAMPLE B 336 grams of polyoxypropylene triol and 80 grams of isophthaloyl biscaprolactam were combined in a reactor and stirred at 150° C. for 24 hours. Initially, after 7 hours the degree of conversion was 77.8% and after 24 hours it had increased to 80%.

EXAMPLE VII 84 grams of polyoxypropylene triol, 20 grams of isophthaloyl biscaprolactam and 3.1 grams of pyrrolidone were combined in a reactor and were stirred at 150° C. for 24 hours. Initially, after 7 hours, the degree of conversion was 90% and after 24 hours it had increased to 95%.

EXAMPLE VIII 336 grams of EO capped polyoxypropylene triol (MW 4480), 75 grams of isophthaloyl biscaprolactam and 5 grams of isophthaloyl bispyrrolidone were heated in a reactor for 24 hours at 140° C. Initially, after 7 hours, the degree of conversion was 90% and after 24 hours, it had increased to 94%.

EXAMPLE IX 168 grams of EO capped polyoxypropylene triol (MW 4480), 37.5 grams of isophthaloyl biscaprolactam and 2.5 grams of isophthaloyl caprolactam pyrrolidone were heated in a reactor for 24 hours at 140° C. Initially, after 7 hours the degree of conversion was 90% and after 24 hours, it had increased to 94%.

EXAMPLE X 336 grams of EO capped polyoxyproplene triol (MW 4480), 80 grams of isophthaloyl biscaprolactam and 12.5 grams of caprolactone were heated in a reactor at 140° C. After 7 hours, the degree of conversion was 93%.

EXAMPLE XI 67 grams of EO capped polyoxypropylene triol (MW 4480), 16 grams of isophthaloyl biscaprolactam and 2.5 grams of valerolactam were heated in a reactor at 140° C. After 7 hours, the degree of conversion amounted to 91%.

EXAMPLE XII 84 grams of EO capped polyoxypropylene triol (MW 4480), 20 grams of isophthaloyl biscaprolactam and 3.1 grams of butyrolactone were heated at 140° C. After 7 hours the degree of conversion was 90%.

COMPARATIVE EXAMPLE C 80 grams of isophthaloyl biscaprolactam (IBC) and 375 grams of Jeffamine T 5000 (Texaco) were heated at 140° C. with stirring. After 5 hours the degree of IBC conversion was 82%.

EXAMPLE XIII 80 grams of IBC and 375 grams of Jeffamine T 5000 were heated at 140° C., with stirring, and then 10 grams of pyrrolidone was added. After 5 hours the degree of IBC conversion was 94%.

We claim:

1. A process for the condensation of imides and alcohols or amines to form ester acyl lactams, amide acyl lactams or ester amide acyl lactams comprising the steps of reacting a polyol or a polyamine, in the liquid phase, with an acyl lactam, and condensing in the presence of a lactone or a lactam with fewer than 7 ring atoms or a compound containing a lactam group with fewer than 7 ring atoms.

2. Process according to claim 1, wherein said condensation is carried out in the presence of at least one of pyrrolidone, caprolactone, 3-methylpyrrolidone, butyrolactone, N-methyl-pyrrolidone, valerolactam, isophthaloyl caprolactam pyrrolidone and isophthaloyl bispyrrolidone.

3. Process according to claim 1, wherein said condensation is carried out in the presence of pyrrolidone.

4. Process according to claim 1, wherein between 0.01 and 15 wt. % of said lactam or said lactone based upon the total weight of reactants is used.

5. Process according to claim 4, wherein between 0.1 and 10 wt. % of said lactam or said lactone based upon the total weight of reactants is used.

6. Process according to claim 4, wherein 1 and 5 wt. % of said lactam or said lactone based upon the total weight of reactants is used.

7. Process according to claim 1, wherein said reaction is carried out at temperature ranges from about 80° C. to about 150° C.

8. Process according to claim 5, wherein between 1 and 5 wt. % of said lactam or said lactone based upon the total weight of reactants is used.

9. The process of claim 1 wherein compounds of the following formula are formed:

A—[D—(—L—)p—Y—Ra—(Y'—L)b]q in which:
D is an oxygen atom or an NH group,
A is a radical formed from a polyol or a polyamine with the formula A—(DH)q in which
q is a number greater than or equal to 2,
p is a number greater than or equal to 0,
(—L—) is an open lactam (block),
L is a lactam ring,
Y and Y' are each acyl groups,
R is an alkyl, aralkyl, alkylaryl ar aryl group which is straight chained, branched or cyclic,
a is a number greater than or equal or 0, and
b is a number greater than or equal to 1.

10. The process of claim 1 wherein the ployol has the following formula:

A—(OH)q in which:
q is a number greater than or equal to 2, and
A is a hydrocarbon, a polyether or a polysiloxane group.

11. The process of claim 1 wherein the polyamine has an average molecular weight of between 300 and 10,000.

12. The process of claim 1 wherein the acyl lactam has the following formula:

L—Y—Ra—(Y'—L)b in which:
L is a lactam ring, and
Y and Y' are both acyl groups,
R is an alkyl, aralkyl, alkylaryl or aryl group which is straight chained, branched or cyclic,
a is a number greater than or equal to 0, and
b is a number greater than or equal to 1.

* * * * *